United States Patent
Lerestif et al.

(10) Patent No.: US 8,536,365 B2
(45) Date of Patent: Sep. 17, 2013

(54) PROCESS FOR THE RESOLUTION OF ENANTIOMERS OF (3,4-DIMETHOXY-BICYCLO[4.2.0]OCTA-1,3,5-TRIEN-7-YL) NITRILE AND APPLICATION IN THE SYNTHESIS OF IVABRADINE

(75) Inventors: Jean-Michel Lerestif, Yvetot (FR); Jean-Pierre Lecouve, Le Havre (FR); Daniel Dron, Sainte Marguerite sur Mer (FR); Eric Gojon, Gonfreville-Caillot (FR); Maryse Phan, Le Havre (FR)

(73) Assignee: Les Laboratoires Servier, Suresnes Cedex (FR)

( * ) Notice: Subject to any disclaimer, the term of this patent is extended or adjusted under 35 U.S.C. 154(b) by 796 days.

(21) Appl. No.: 12/583,632

(22) Filed: Aug. 24, 2009

(65) Prior Publication Data

US 2010/0056778 A1    Mar. 4, 2010

(30) Foreign Application Priority Data

Aug. 29, 2008   (FR) ...................... 08 04755

(51) Int. Cl.
*C07C 255/00*   (2006.01)

(52) U.S. Cl.
USPC ........................................................ 558/354

(58) Field of Classification Search
None
See application file for complete search history.

(56) References Cited

U.S. PATENT DOCUMENTS

| | | |
|---|---|---|
| 5,296,482 A | 3/1994 | Peglion et al. |
| 2005/0261376 A1* | 11/2005 | Lerestif et al. ................ 514/649 |

FOREIGN PATENT DOCUMENTS

| | | |
|---|---|---|
| EP | 0534 859 | 3/1993 |
| WO | 2005/110993 | 11/2005 |

OTHER PUBLICATIONS

Welch et al., Chiral Chromatography in Support of Pharmaceutical Process Research, in Preparative Enantioselective Chromatography, (G. B. Cox ed., Blackwell Publishing 2005) pp. 54-63.*
"Stereochemistry in Drug Design" inTextbook of Drug Design and Discovery ,Third edition, Povl Krogsgaard-Larsen et al., 2002, Taylor & Francis pp. 1-18.*
C. Perrin, et al., "screening approach for chiral separation of pharmaceuticals part I. Normal-phase liquid chromatography" Journal of Chromatography, vol. 947, No. 1, p. 69-83, 2002.
French Preliminary Search Report for FR0804775 of Mar. 23, 2009.

* cited by examiner

*Primary Examiner* — Karl J Puttlitz
(74) *Attorney, Agent, or Firm* — Hueschen and Sage

(57) ABSTRACT

Process for the optical resolution of the compound of formula (I):

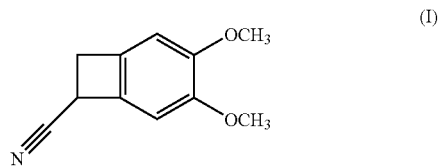

by chiral chromatography.
Application in the synthesis of ivabradine, of its addition salts with a pharmaceutically acceptable acid and of their hydrates.

12 Claims, No Drawings

PROCESS FOR THE RESOLUTION OF ENANTIOMERS OF (3,4-DIMETHOXY-BICYCLO[4.2.0]OCTA-1,3,5-TRIEN-7-YL) NITRILE AND APPLICATION IN THE SYNTHESIS OF IVABRADINE

The present invention relates to a process for the optical resolution of (3,4-dimethoxybicyclo[4.2.0]octa-1,3,5-trien-7-yl)nitrile of formula (I) and to the application thereof in the synthesis of ivabradine, of its addition salts with a pharmaceutically acceptable acid and of their hydrates.

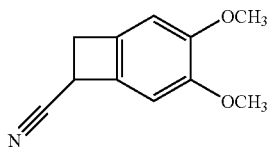
(I)

Ivabradine of formula (II):

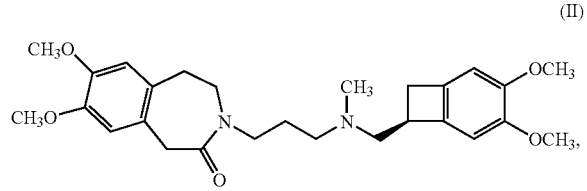
(II)

or 3-{3-[{[(7S)-3,4-dimethoxybicyclo[4.2.0]octa-1,3,5-trien-7-yl]methyl} (methyl)amino]-propyl}-7,8-dimethoxy-1,3,4,5-tetrahydro-2H-3-benzazepin-2-one, and its addition salts with a pharmaceutically acceptable acid, and more especially its hydrochloride, have very valuable pharmacological and therapeutic properties, especially bradycardic properties, making these compounds useful in the treatment or prevention of various clinical situations of myocardial ischaemia such as angina pectoris, myocardial infarct and associated rhythm disturbances, and also in various pathologies involving rhythm disturbances, especially supraventricular rhythm disturbances, and in heart failure.

The preparation and therapeutic use of ivabradine and its addition salts with a pharmaceutically acceptable acid, and more especially its hydrochloride, have been described in the European patent specification EP 0 534 859.

That patent specification describes the synthesis of ivabradine starting from the compound of formula (III):

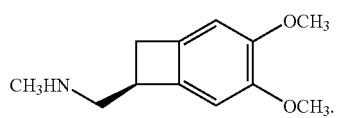
(III)

The compound of formula (III) is prepared starting from the compound of formula (IV):

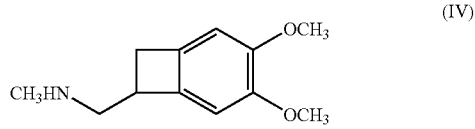
(IV)

by resolution using camphorsulphonic acid.

The compound of formula (III) is an important intermediate in the synthesis of ivabradine.

Resolution of the secondary amine of formula (IV) results in the compound of formula (III) in only a low yield (4 to 5%).

However, in view of the pharmaceutical importance of ivabradine and its salts, it has been imperative to be able to obtain the compound of formula (III) using an effective industrial process and, especially, in a good yield and with excellent chemical and enantiomeric purity.

The Applicant has developed a process for the optical resolution of the compound of formula (I) which makes it possible to obtain the compound of formula (III) with good characteristics of yield and chemical and enantiomeric purity. The process of the invention makes it possible to obtain the target enantiomer of the compound of formula (I) in an excellent enantiomeric excess, with high productivity and in an excellent yield whilst economising on the solvents used.

More specifically, the present invention relates to a process for the optical resolution of (3,4-dimethoxy-bicyclo[4.2.0]octa-1,3,5-trien-7-yl)nitrile of formula (I):

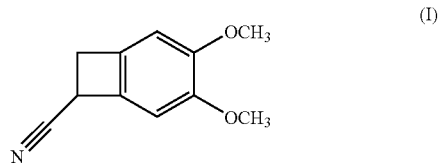 [SMILES: COc1cc2c(cc1OC)C(C#N)C2]
(I)

to yield its enantiomers of absolute configuration (S) and (R), respectively of formula (Ia) and (Ib):

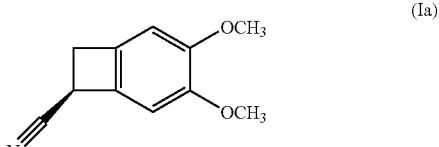
(Ia)

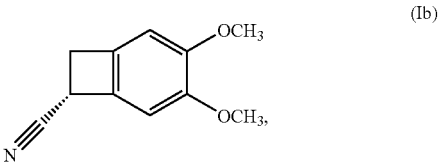
(Ib)

wherein a racemic or enantiomerically enriched mixture of (3,4-dimethoxy-bicyclo[4.2.0]octa-1,3,5-trien-7-yl)nitrile is separated into its two enantiomers, (S)-(3,4-dimethoxy-bicyclo[4.2.0]octa-1,3,5-trien-7-yl)nitrile of formula (Ia) and (R)-(3,4-dimethoxy-bicyclo[4.2.0]octa-1,3,5-trien-7-yl)nitrile of formula (Ib), by chiral chromatography.

Optical resolution is understood to mean the separation of the two enantiomers of a racemic mixture or of any mixture of those two enantiomers.

A racemic mixture is understood to mean a mixture of two enantiomers in a ratio of from 55:45 to 45:55, preferably in a ratio of 50:50.

An enantiomerically enriched mixture is understood to mean a mixture of two enantiomers containing significantly more of one of the enantiomers in a ratio varying between 55:45 and 90:10.

Chiral chromatography is understood to mean the arrangement making possible the separation of the enantiomers of a mixture by means of a chiral stationary phase and a mobile phase composed of a solvent or of a mixture of solvents.

In accordance with a preferred embodiment of the invention, a continuous multi-column separation process is used.

In accordance with an even more preferred embodiment of the invention, a simulated moving bed chromatography process is used.

Simulated moving bed chromatography is understood to mean a continuous chromatography process which makes it possible to simulate movement of the stationary phase in the opposite direction to the movement of the mobile phase. Such a process makes it possible to separate compounds that are difficult or impossible to separate by conventional chromatography techniques. When a chiral stationary phase is used, such a process is especially useful for the separation of enantiomers. Use of simulated moving bed chromatography makes it possible to carry out continuous resolution of a mixture of enantiomers with high productivity, whilst reducing the amounts of stationary and mobile phases used compared with discontinuous chromatography processes.

In accordance with one of the preferred embodiments of the invention, the stationary phase used for the chiral chromatography comprises a silica gel impregnated with a functionalised polysaccharide.

In accordance with a preferred embodiment of the invention, the stationary phase used for the chiral chromatography comprises a cellulose or amylose derivative of tris(4-methylbenzoate) or of tris(3,5-dimethylphenylcarbamate).

A mobile phase preferably used for the chiral chromatography comprises an alcohol, another organic solvent or a mixture of an alcohol and another organic solvent.

Among the alcohols that may be used for the chiral chromatography there may be mentioned, without implying any limitation, isopropanol, ethanol and methanol.

An alcohol preferably used for the chiral chromatography is isopropanol.

Among the organic solvents that may be used for the chiral chromatography there may be mentioned, without implying any limitation, heptane, hexane, cyclohexane, acetonitrile and methyl tert-butyl ether.

An organic solvent preferably used is heptane or hexane.

The mobile phase used for the chiral chromatography preferably comprises a mixture of an alcohol and another organic solvent.

A mobile phase even more preferably used for the chiral chromatography comprises a mixture of isopropanol and heptane or a mixture of isopropanol and hexane.

In a preferred embodiment of the invention, the mobile phase used for the chiral chromatography comprises a mixture of isopropanol and heptane or a mixture of isopropanol and hexane in a ratio varying from 50:50 to 2:98.

In accordance with a preferred embodiment of the invention, the mobile phase used for the chiral chromatography is recycled.

The chiral chromatography is preferably carried out at a temperature from 15° C. to 40° C. inclusive.

In accordance with a preferred embodiment of the invention, the optical resolution is carried out on a racemic mixture of (3,4-dimethoxy-bicyclo[4.2.0]octa-1,3,5-trien-7-yl)nitrile of formula (I).

In accordance with one of the preferred embodiments of the invention, the target enantiomer of (3,4-dimethoxy-bicyclo[4.2.0]octa-1,3,5-trien-7-yl)nitrile is (S)-(3,4-dimethoxy-bicyclo[4.2.0]octa-1,3,5-trien-7-yl)nitrile of formula (Ia).

In accordance with one of the preferred embodiments of the invention, the (R) enantiomer of (3,4-dimethoxy-bicyclo[4.2.0]octa-1,3,5-trien-7-yl)nitrile, of formula (Ib), is racemised and used as starting material in the optical resolution process.

The compound of formula (Ia) may yield the compound of formula (V):

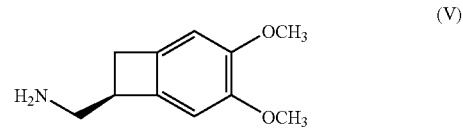 [SMILES: COc1cc2c(cc1OC)[C@@H](CN)C2]

(V)

by means of a reduction reaction.

The reduction of the compound of formula (Ia) is preferably carried out in the presence of palladium-on-carbon and HCl under a hydrogen atmosphere or in the presence of sodium tetraborohydride and trifluoroacetic acid.

The compound of formula (V) obtained by reduction of the compound of formula (Ia) is useful in the synthesis of ivabradine of formula (II).

By way of example, the compound of formula (V) is converted into the carbamate of formula (VI):

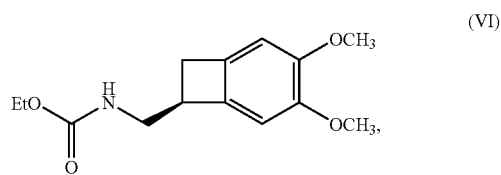

(VI)

which is reduced to form the compound of formula (III):

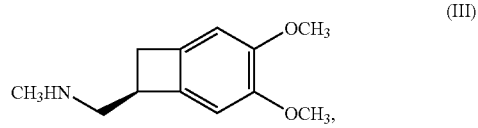

(III)

which is converted into ivabradine of formula (II)

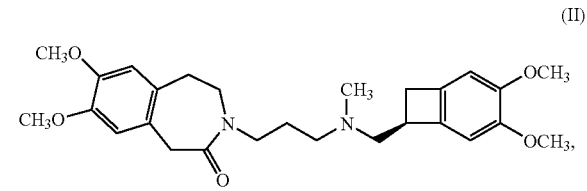

(II)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, which may optionally be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, or into a hydrate thereof.

Among the known methods for carrying out the conversion of the compound of formula (III) into ivabradine there may be mentioned those described in the European patent specifications EP 0 534 859 and EP 1 589 005.

The compounds of formulae (Ia) and (Ib) are new products which are useful as synthesis intermediates in the chemical or pharmaceutical industry, especially in the synthesis of ivabradine, of its addition salts with a pharmaceutically acceptable acid and of hydrates thereof, and by virtue thereof they form an integral part of the present invention.

List of Abbreviations Used

DBU: 1,8-diazabicyclo[5.4.0]undec-7-ene
eq.: equivalent
TFA: trifluoroacetic acid
THF: tetrahydrofuran The Examples hereinbelow illustrate the invention.

EXAMPLE 1

Separation of the Enantiomers of (3,4-dimethoxy-bicyclo[4.2.0]octa-1,3,5-trien-7-yl)nitrile by Preparative Chiral Chromatography Dissolve 480 mg of compound of formula (I) in 5 mL of methanol, inject onto a Prochrom 50 cm×50 mm column, packed up to 25 cm with 300 g of Chiracel OJ phase, at a flow rate of 80 mL/min and elute at that flow rate in a mixture of heptane/isopropanol (70/30).

The enantiomer of formula (Ia) (configuration (S)) is obtained in a yield of 45.6% and with an enantiomeric purity of 97.6%.

The enantiomer of formula (Ib) (configuration (R)) is obtained in a yield of 42.2% and with an enantiomeric purity of 99.3%.

EXAMPLE 2

[(7S)-3,4-dimethoxybicyclo[4.2.0]octa-1,3,5-trien-7-yl]methanamine by Means of Reduction of (S)-(3,4-dimethoxy-bicyclo[4.2.0]octa-1,3,5-trien-7-yl)nitrile in the Presence of NaBH$_4$ Introduce NaBH$_4$ (3 eq.) and THF (10 mL/g) into a three-necked 125 mL flask placed under nitrogen sweeping and provided with a condenser, a magnetic bar, a CaCl$_2$ guard on the nitrogen inlet and a temperature probe. Pour in TFA (2.97 eq.) dropwise at 20-25° C. Add (S)-(3,4-dimethoxy-bicyclo[4.2.0]octa-1,3,5-trien-7-yl)nitrile (1 eq.) solution in THF (4 mL/g) dropwise. Stir at 20-25° C. overnight, then pour the reaction mixture into aqueous 0.3M HCl solution (0.5 eq.) and stir at 20-25° C. for 1 hour. Filter through a frit under vacuum, rinse with THF and evaporate off the solvent under reduced pressure. Take up the crude reaction product in dichloromethane (20 mL/g), add 10 mL/g of water and sodium hydroxide solution (2 mL/g). Stir for 15 minutes and then allow to separate; wash the organic phase with water, dry over MgSO$_4$ and evaporate off the solvent under reduced pressure to yield the title product in a yield of 78.8% and with an enantiomeric purity of 94.4%.

EXAMPLE 3

[(7S)-3,4-dimethoxybicyclo[4.2.0]octa-1,3,5-trien-7-yl]methanamine by Means of Reduction of (S)-(3,4-dimethoxy-bicyclo[4.2.0]octa-1,3,5-trien-7-yl)nitrile in the Presence of palladium-on-carbon Introduce 1 eq. of (S)-(3,4-dimethoxy-bicyclo[4.2.0]octa-1,3,5-trien-7-yl)nitrile, 1 eq. of methanolic HCl 1.12N and 0.1% by weight of 5% palladium-on-carbon into a 125 mL autoclave. Rinse with methanol (10 mL/g). Purge with nitrogen and then with hydrogen, stir at 20° C. and hydrogenate under 30 bars at that temperature for 5 hours. Release the autoclave pressure, filter the reaction mixture and distil off the solvents under reduced pressure. Take up the resulting hydrochloride in dichloromethane (20 mL/g), add 10 mL/g of water and sodium hydroxide solution (2 mL/g). Stir for 15 minutes and then allow to separate, wash the organic phase with water, dry over MgSO$_4$ and evaporate off the solvent under reduced pressure to yield the title product in a yield of 90% and with an enantiomeric purity of 95.5%.

EXAMPLE 4

Racemic (3,4-dimethoxy-bicyclo[4.2.0]octa-1,3,5-trien-7-yl)nitrile by Means of Racemisation of (R)-(3,4-dimethoxy-bicyclo[4.2.0]octa-1,3,5-trien-7-yl)nitrile Introduce 100 mg of (R)-(3,4-dimethoxy-bicyclo[4.2.0]octa-1,3,5-trien-7-yl)nitrile (0.53 mmol), 5 mL of isopropanol and 121 mg of DBU (1.5 eq.) into a flask provided with a condenser and with magnetic stirring. Heat at 65° C. for 2 hours and then allow to return to ambient temperature. Filter to obtain the title compound.

The invention claimed is:
1. A process for the optical resolution of (3,4-dimethoxy-bicyclo[4.2.0]octa-1,3,5-trien-7-yl)nitrile of formula (I):

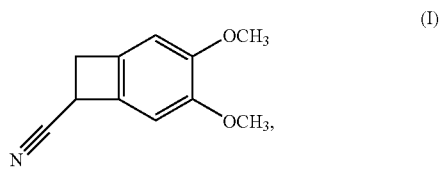

wherein a racemic or enantiomerically enriched mixture of (3,4-dimethoxy-bicyclo[4.2.0]octa-1,3,5-trien-7-yl)nitrile is separated into its two enantiomers (S)-(3,4-dimethoxy-bicyclo[4.2.0]octa-1,3,5-trien-7-yl)nitrile of formula (Ia):

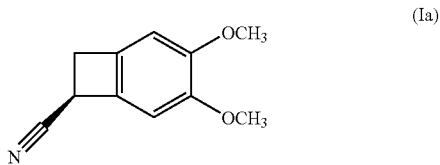 [SMILES: COc1cc2c(cc1OC)[C@@H](C#N)C2]

and (R)-(3,4-dimethoxy-bicyclo[4.2.0]octa-1,3,5-trien-7-yl)nitrile of formula (Ib):

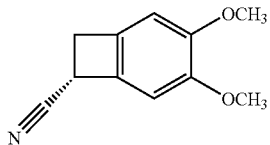
(Ib)

by chiral chromatography comprising a stationary phase and a mobile phase, wherein the stationary phase comprises a silica gel impregnated with a functionalised polysaccharide and wherein the mobile phase comprises a mixture of an alcohol and another organic solvent, wherein the organic solvent is heptane or hexane.

2. The process of claim 1, wherein the optical resolution comprises a continuous multi-column separation process.

3. The process of claim 1, wherein the optical resolution comprises a simulated moving bed chromatography process.

4. The process of claim 1, wherein the stationary phase used for the chiral chromatography comprises a cellulose or amylose derivative of tris(4-methylbenzoate) or of tris(3,5-dimethylphenylcarbamate).

5. The process of claim 1, wherein the alcohol is isopropanol.

6. The process of claim 1, wherein the mobile phase comprises a mixture of isopropanol and heptane or a mixture of isopropanol and hexane.

7. The process of claim 6, wherein the mobile phase comprises a mixture of isopropanol and heptane or a mixture of isopropanol and hexane in a ratio varying from 50:50 to 2:98.

8. The process of claim 1, wherein the mobile phase used for the chiral chromatography is recycled.

9. The process of claim 1, wherein the chiral chromatography is carried out at a temperature from 15° C. to 40° C. inclusive.

10. The process of claim 1, wherein the optical resolution is carried out on a racemic mixture of (3,4-dimethoxy-bicyclo[4.2.0]octa-1,3,5-trien-7-yl)nitrile of formula (I).

11. The process of claim 1, wherein the target enantiomer of (3,4-dimethoxy-bicyclo[4.2.0]octa-1,3,5-trien-7-yl)nitrile is (S)-(3,4-dimethoxy-bicyclo[4.2.0]octa-1,3,5-trien-7-yl)nitrile of formula (Ia):

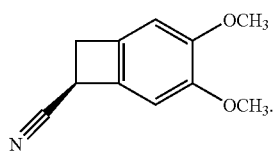
(Ia)

12. The process of claim 1, wherein the (R) enantiomer of (3,4-dimethoxy-bicyclo[4.2.0]octa-1,3,5-trien-7-yl)nitrile of formula (Ib)

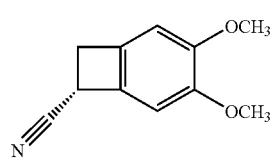
(Ib)

is racemised and used as starting material in the optical resolution process.

* * * * *